United States Patent [19]

Metzger et al.

[11] 4,154,597
[45] May 15, 1979

[54] 3-(1,3,4-THIADIAZOL-2-YL)-5-ACYLOXY (-CARBAMOYLOXY)-HYDANTOIN COMPOUNDS AND HERBICIDAL COMPOSITIONS

[75] Inventors: Carl Metzger, Wuppertal; Ludwig Eue; Robert R. Schmidt, both of Cologne, all of Fed. Rep. of Germany

[73] Assignee: Bayer Aktiengesellschaft, Leverkusen, Fed. Rep. of Germany

[21] Appl. No.: 804,026

[22] Filed: Jun. 6, 1977

Related U.S. Application Data

[63] Continuation of Ser. No. 639,958, Dec. 11, 1975, abandoned, which is a continuation of Ser. No. 432,004, Jan. 9, 1974, abandoned.

[30] Foreign Application Priority Data

Jan. 13, 1973 [DE] Fed. Rep. of Germany ........ 2301703

[51] Int. Cl.² .................. A01N 9/12; C07D 417/04
[52] U.S. Cl. .................................. 71/90; 260/306.8 D
[58] Field of Search ........................ 71/90; 260/306.8 D

[56] References Cited

U.S. PATENT DOCUMENTS

| | | | |
|---|---|---|---|
| 3,758,492 | 9/1973 | Metzger et al. | 260/306.8 D |
| 3,787,432 | 1/1974 | Krenzer | 71/90 |
| 3,843,670 | 10/1974 | Moser et al. | 260/306.8 D |
| 3,849,432 | 11/1974 | Metzger et al. | 260/306.8 D |
| 3,925,403 | 12/1975 | Krenzer | 71/90 |

OTHER PUBLICATIONS

Gulf, *Abstract of NL*7105077, Apr. 15, 1971.
Kubo, *Report Delivered at Seminar,* N.C. State, Raleigh, North Carolina, Mar. 19, 1969.

*Primary Examiner*—Alton D. Rollins
*Attorney, Agent, or Firm*—Sprung, Felfe, Horn, Lynch & Kramer

[57] ABSTRACT

3-(1,3,4-thiadiazol-2-yl)-5-acyloxy(carbamoyloxy)-hydantoin compounds of the formula:

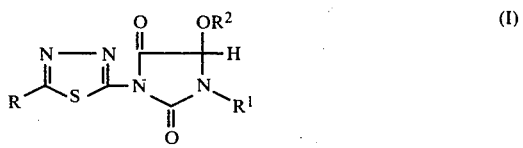

in which
R is alkyl, haloalkyl, alkylmercapto or alkylsulfonyl,
R¹ is alkyl, and
R² is alkylcarbonyl, alkoxycarbonyl, alkylcarbamoyl or optionally substituted arylcarbonyl;

are remarkably active as herbicides and are particularly useful as selective herbicides in cotton cultivations or in cereal crops, including corn.

8 Claims, No Drawings

3-(1,3,4-THIADIAZOL-2-YL)-5-ACYLOXY(CARBAMOYLOXY)-HYDANTOIN COMPOUNDS AND HERBICIDAL COMPOSITIONS

This is a continuation of Ser. No. 639,958, filed Dec. 11, 1975, which in turn was a continuation of Ser. No. 432,004, filed Jan. 9, 1974, both now abandoned.

The present invention relates to certain new 3-(1,3,4-thiadiazol-2-yl)-5-acyloxy(carbamoyloxy)-hydantoin compounds, to compositions containing them and to their use as herbicides.

It is known that 3-methyl-1-phenyl-5-methylcarbamoyloxy-hydantoin can be used for combating weeds; (see German Offenlegungsschrift, DOS 2,053,211). However, this action is not always entirely satisfactory, if low amounts and low concentrations are used.

The present invention provides 5-acyloxy(carbamoyloxy)-hydantoin compounds of the formula

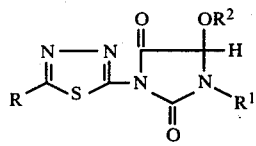

(I)

in which

R is alkyl, haloalkyl, alkylmercapto or alkylsulfonyl,
$R^1$ is alkyl, and
$R^2$ is alkylcarbonyl, alkoxycarbonyl, alkylcarbamoyl or optionally substituted arylcarbonyl.

Surprisingly, the 5-acryloxy(carbamoyloxy)-hydantoins according to the invention display a greater herbicidal potency than the known 3-methyl-1-phenyl-5-methylcarbamoyloxyhydantoin, which is chemically the nearest active compound. They thus represent an enrichment of the art.

R preferably represents straight-chain or branched alkyl of from 1 to 6 carbon atoms, especially of from 3 to 5 carbon atoms, haloalkyl of from 1 to 3 carbon atoms and 2 to 7 halogen atoms, especially fluorine, alkylmercapto of from 1 to 6 carbon atoms, especially of from 1 to 4 carbon atoms, or alkylsulfonyl of from 1 to 6 carbon atoms, especially of from 1 to 4 carbon atoms. The following radicals may be mentioned as examples of R: propyl, isopropyl, tert.-butyl, butyl, isobutyl, sec.-butyl, trifluoromethyl, pentafluoroethyl, ethylmercapto, methylmercapto, propylmercapto, isopropylmercapto, butylmercapto, isobutylmercapto, sec.-butylmercapto, methylsulfonyl, ethylsulfonyl, propylsulfonyl, isopropylsulfonyl, butylsulfonyl, isobutylsulfonyl and sec.-butylsulfonyl.

$R^1$ preferably represents straight-chain or branched alkyl of from 1 to 5 carbon atoms, especially of from 1 or 2 carbon atoms. The methyl and ethyl radicals may be mentioned as examples.

$R^2$ preferably represents straight-chain or branched alkylcarbonyl of from 1 to 6 carbon atoms, especially of from 1 to 4 carbon atoms in the alkyl moiety, alkoxycarbonyl of from 1 to 4 carbon atoms, especially of from 1 to 3 carbon atoms in the alkoxy moiety, (methyl, ethyl, propyl, isopropyl, butyl, sec.-butyl, isobutyl, methoxy, ethoxy and propoxy radicals may be mentioned as examples of alkyl and alkoxy moieties), arylcarbonyl of from 6 to 10 carbon atoms, especially of from 6 carbon atoms in the aryl moiety, which can optionally be monosubstituted or polysubstituted by alkyl of from 1 to 3 carbon atoms, especially methyl, or by halogen, especially chlorine, or straight-chain or branched alkylcarbamoyl of from 1 to 6 carbon atoms, especially of from 1 to 4 carbon atoms in the alkyl moiety, (propyl, ethyl and methyl may be mentioned as examples of the alkyl moiety).

The invention also provides a process for the production of a 3-(1,3,4-thiadiazol-2-yl)-5-acyloxy(carbamoyloxy)-hydantoin of the formula (I) in which (a) a 3-(1,3,4-thiadiazol-2-yl)-5-hydroxyhydantoin of the general formula

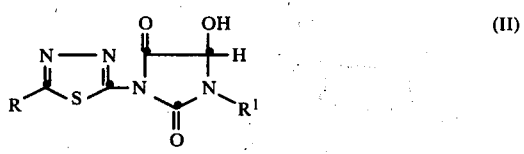

(II)

in which

R and $R^1$ have the abovementioned meanings is reacted with a carboxylic acid halide or carbonic acid halide of the general formula

$R^3$—CO—Hal        (III)

in which $R^3$ represents alkyl or alkoxy and
Hal represents halogen (especially chlorine), optionally in the presence of an acid-binding agent and in the presence of a solvent, or (b) a 3-(1,3,4-thiadiazol-2-yl)-5-hydroxyhydantoin of the general formula (II) is reacted with an isocyanate of the general formula

$R^4$—N=C=O        (IV)

in which $R^4$ represents alkyl, optionally in the presence of a solvent, or (c) a 3-(1,3,4-thiadiazol-2-yl)-5-hydroxy-hydantoin of the general formula (II) is reacted with a carboxylic acid anhydride of the general formula

$R^4$—CO—O—CO—$R^4$        (V)

in which $R^4$ has the abovementioned meaning, optionally in the presence of a solvent and using base catalysis.

If 1-methyl-3-(5-tert.-butyl-1,3,4-thiadiazol-2-yl)5-hydroxy-hydantoin and propionyl chloride are used as starting compounds, the course of the reaction in process variant (a) can be represented by the following formula scheme:

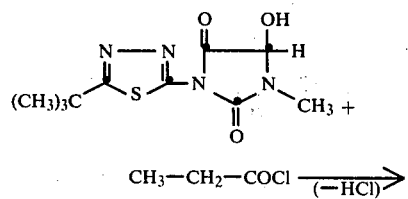

-continued

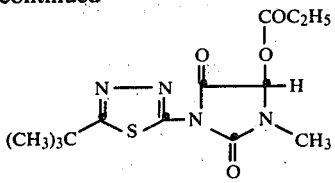

If 1-methyl-3-(5-trifluoromethyl-1,3,4-thiadiazol-2-yl)-5-hydroxy-hydantoin and methylisocyanate are used as starting compounds, the course of the reaction in process variant (b) can be represented by the following formula scheme:

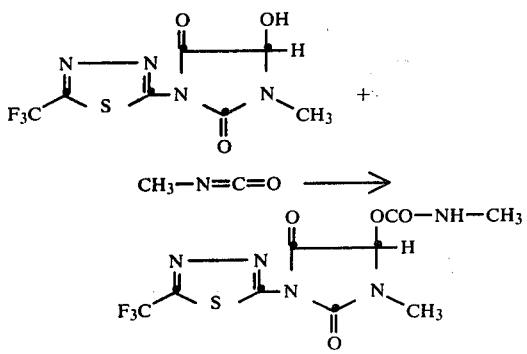

If 1-methyl-3-(5-propylmercapto-1,3,4-thiadiazol2-yl)-5-hydroxy-hydantoin and acetic acid are used as starting compounds, the course of the reaction in process variant (c) can be represented by the following formula scheme:

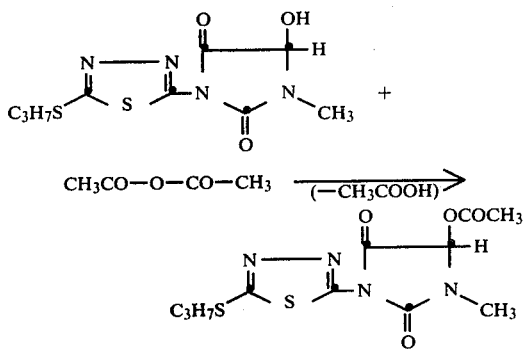

Formula (II) provides a general definition of the 3-(1,3,4-thiadiazol-2-yl)-5-hydroxy-hydantoins which can be used in the process of the invention.

The 3-(1,3,4-thiadiazol-2-yl)-5-hydroxy-hydantoins which can be used in the process according to the invention were not previously known; however, they form the subject of a separate patent application, viz., German Patent Application No. P 23 01 704.1. They can be prepared by reacting parabanic acid derivatives of the formula (VI)

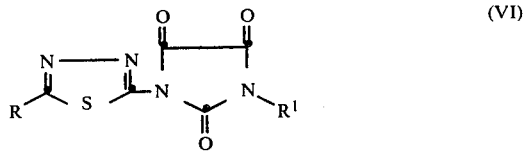

in which

R and $R^1$ have the abovementioned meanings with hydrogen in the presence of a catalyst, such as palladium, and optionally of an aqueous acid or base, or with a hydrogen donor, such as sodium borohydride or lithium aluminum hydride, in the presence of a polar solvent, for example an alcohol, at a temperature from $-20°$ C. to $+20°$ C. (compare also some of the Examples at the end of the present text).

The following may be mentioned individually as examples of the 3-(1,3,4-thiadiazol-2-yl)-5-hydroxy-hydantoins which can be used in the process of the invention: 1-methyl-3-(5-isopropyl-1,3,4-thiadiazol-2-yl)-5-hydroxy-hydantoin, 1-methyl-3-(5-tert.-butyl-1,3,4-thiadiazol-2-yl)-5-hydroxyhydantoin, 1-ethyl-3-(5-tert.-butyl-1,3,4-thiadiazol-2-yl)-5-hydroxy-hydantoin, 1-methyl-3-(5-trifluoromethyl-1,3,4-thiadiazol-2-yl)-5-hydroxy-hydantoin, 1-ethyl-3-(5-trifluoromethyl-1,3,4-thiadiazol-2-yl)-5-hydroxy-hydantoin, 1-methyl-3-(5-methyl-mercapto-1,3,4-thiadiazol-2-yl)-5-hydroxy-hydantoin, 1-methyl-3-(5-ethylmercapto-1,3,4-thiadiazol-2-yl)-5-hydroxy-hydantoin, 1-methyl-3-(5-propylmercapto-1,3,4-thiadiazol-2-yl)-5-hydroxyhydantoin, 1-methyl-3-(5-isopropylmercapto-1,3,4-thiadiazol-2-yl)-5-hydroxy-hydantoin, 1-methyl-3-(5-butyl-mercapto-1,3,4-thiadiazol-2-yl)-5-hydroxy-hydantoin, 1-methyl-3-(5-isobutylmercapto-1,3,4-thiadiazol-2-yl)-5-hydroxy-hydantoin, 1-methyl3-(5-sec.-butylmercapto-1,3,4-thiadiazol-2-yl)-5-hydroxyhydantoin, 1-methyl-3-(5-methylsulfonyl-1,3,4-thiadiazol-2-yl)-5-hydroxy-hydantoin, 1-methyl-3-(5-ethylsulfonyl-1,3,4-thiadiazol-2-yl)-5-hydroxy-hydantoin, 1-methyl-3-(5-propylsulfonyl-1, 3,4-thiadiazol-2-yl)-5-hydroxy-hydantoin, 1-methyl-3-(5-isopropylsulfonyl-1,3,4-thiadiazol-2-yl)-5-hydroxy-hydantoin, 1-methyl-3-(5-butylsulfonyl-1,3,4-thiadiazol-2-yl)-5-hydroxyhydantoin, 1-methyl-3-(5-isobutylsulfonyl-1,3,4-thiadiazol-2-yl)-5-hydroxy-hydantoin and 1-methyl-3-(5-sec.-butylsulfonyl-1, 3,4-thiadiazol-2-yl)-5-hydroxy-hydantoin.

Of the starting compounds used, the carboxylic acid halides and carbonic acid halides are generally defined by the formula (III), the isocyanates by the formula (IV) and the carboxylic acid anhydrides by the formula (V).

The following may be mentioned individually as examples of the carboxylic acid halides, carbonic acid halides, carboxylic acid anhydrides and isocyanates which can be used in the process of the invention: benzoyl chloride, acetyl chloride, propionyl chloride, pivaloyl chloride, valeroyl chloride, isobutyric acid chloride, chloroformic acid methyl ester, chloroformic acid ethyl ester, chloroformic acid propyl ester, chloroformic acid butyl ester, acetic anhydride, propionic anhydride, butyric anhydride, methylisocyanate, ethylisocyanate, propylisocyanate and isopropylisocyanate.

The starting compounds of formulae (III), (IV) and (V) are known.

All inert organic solvents can be used as diluents in the reaction of the invention according to process variant (a). Preferred solvents include hydrocarbons such as benzene, ligroin, petroleum ether, esters, such as acetic acid ethyl ester, acetoacetic acid ethyl ester, acetic acid butyl ester and acetic acid methyl ester, and ethers such as diethyl ether, dibutyl ether, dioxan and tetrahydrofuran.

All customary acid-binding agents can be used as the acid binders in process variant (a). Preferred agents include the alkali metal hydroxides, alkali metal carbonates, alkaline earth metal hydroxides and tertiary organic bases. The following may be mentioned individually as being particularly suitable: calcium carbonate, magnesium carbonate, sodium hydroxide, triethylamine and pyridine.

The reaction temperatures in process variant (a) can be varied over a wide range. In general, a temperature from −10° to +30° C., preferably 0° to +30° C., is used. The reaction is generally carried out under normal pressure.

In carrying out process variant (a), about 1 mol of carboxylic acid halide of formula (III) and about 1 mol of acid-binding agent are generally employed per mol of hydroxyhydantoin of formula (II).

To isolate the compound of formula (I), the halide produced may be filtered off, the organic solvent removed by distillation in vacuo and the residue purified by recrystallization.

Diluents which can be used for the reaction of process variant (b) are inert organic solvents, preferably those mentioned for process variant (a).

The reaction temperatures in process variant (b) can be varied within a wide range. In general, the reaction is carried out at from 30° to 100° C., preferably 30° to 80° C., and under normal pressure.

In carrying out process variant (b), about 1 mol of isocyanate of Formula (IV) is generally employed per mol of hydroxyhydantoin of formula (I).

To isolate the compound of formula (I), the solvent may be removed by distillation and the residue purified by recrystallization.

Diluents which can be used for the reaction of process variant (c) are polar organic solvents. The reaction is, however, preferably carried out without a special solvent.

Preferred acid-binding agents in process variant (c) are tertiary organic bases or alkali metal salts of organic acids which dissociate slightly, the salts displaying a buffer action. Sodium acetate and pyridine may be mentioned individually as being particularly suitable.

The reaction temperatures in process variant (c) can be varied within a wide range. In general, the reaction is carried out at from 50° to 140° C., preferably 90° to 120° C.

The reaction is generally carried out under normal pressure.

In carrying out process variant (c), a 2-fold to 500-fold excess of carboxylic acid anhydride, which simultaneously serves as a solvent, and optionally a 1-fold to 1½-fold excess of acid-binding agent, are generally employed per mol of hydroxyhydantoin of formula (II).

To isolate the compounds of formula (I), the reaction mixture may be poured onto ice water and the excess carboxylic anhydride destroyed by hydrolysis. The resulting water-insoluble precipitate may be filtered off and purified by recrystallization.

The following examples are illustrative of the preparation of the instant compounds:

EXAMPLE 1—Preparation of 1-methyl-3-(5-tert.-butyl-1,3,4-thiadiazol-2-yl)-5-propionyloxy-hydantoin

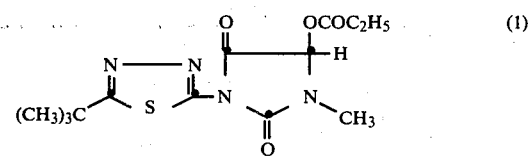

4.6 g (0.05 mol) of propionic acid chloride were slowly added dropwise at 20° C. to a solution of 13.5 g (0.05 mol) of 1-methyl-3-(5-tert.-butyl-1,3,4-thiadiazol-2-yl)-5-hydroxyhydantoin and 5.1 g (0.05 mol) of triethylamine in 200 ml of anhydrous ethyl acetate. After stirring for one hour at 25° C., the triethylamine hydrochloride was filtered off, the filtrate was evaporated and the residue was recrystallized from a mixture of ligroin and ethyl acetate.

14.9 g (91.5% of theory) of 1-methyl-3-(5-tert.-butyl-1,3,4-thiadiazol-2-yl)-5-propionyloxy-hydantoin of melting point 176° C. were obtained.

EXAMPLE 2—Preparation of 1-methyl-3-(5-tert.-butyl-1,3,4-thiadiazol-2-yl)-5-methyl-carbamoyloxy-hydantoin

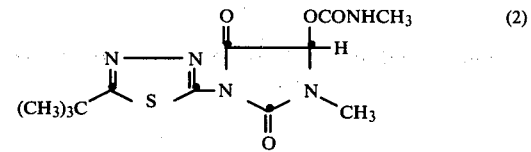

1.5 g (0.026 mol) of methylisocyanate were added dropwise at 30° C. to a suspension of 6.25 g (0.023 mol) of 1-methyl-3-(5-tert.-butyl-1,3,4-thiadiazol-2-yl)-5-hydroxyhydantoin in 100 ml of ethyl acetate. Thereafter the mixture was boiled for 4 hours under reflux. After cooling, the solvent was distilled off in vacuo and the residue was recrystallized from a ligroin/ethyl acetate mixture.

6.4 g (85% of theory) of 1-methyl-3-(5-tert.-butyl-1,3,4-thiadiazol-2-yl)-5-methyl-carbamoyloxy-hydantoin of melting point 165° C. were obtained.

EXAMPLE 3—Preparation of 1-methyl-3-(5-tert.-butyl-1,3,4-thiadiazol-2-yl)-5-acetoxy-hydantoin

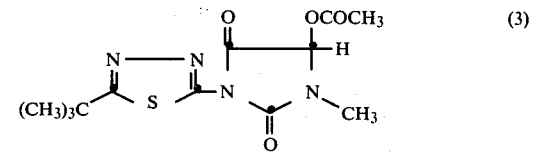

13.5 g (0.05 mol) of 1-methyl-3-(5-tert.-butyl-1, 3,4-thiadiazol-2-yl)-5-hydroxy-hydantoin were heated with 50 ml of acetic anhydride and 1 g of anhydrous Na acetate for 2 hours to 100° C. After cooling, the mixture was poured into 500 ml of water and stirred until the excess anhydride had disappeared. The product was filtered off, dried and recrystallized from methanol.

15.2 g (97.5% of theory) of 1-methyl-3-(5-tert.-butyl-1,3,4-thiadiazol-2-yl)-5-acetoxy-hydantoin of melting point 168° C. were obtained.

EXAMPLES 4–15

The active compounds listed in the table which follows were prepared analogously to Examples 1–3.

Table

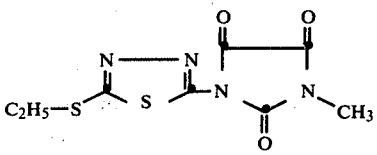

(I)

| Example | R | R¹ | R² | Melting point (°C.) | Process variant |
|---|---|---|---|---|---|
| 4 | t-C$_4$H$_9$ | C$_2$H$_5$ | CH$_3$ | 105 | (c) |
| 5 | t-C$_4$H$_9$ | C$_2$H$_5$ | C$_2$H$_5$ | Oil | (a) |
| 6 | t-C$_4$H$_9$ | C$_2$H$_5$ | OCH$_3$ | 109 | (a) |
| 7 | t-C$_4$H$_9$ | C$_2$H$_5$ | NHCH$_3$ | 145 | (b) |
| 8 | CF$_3$ | CH$_3$ | CH$_3$ | Oil | (c) |
| 9 | CF$_3$ | CH$_3$ | NHCH$_3$ | 65 | (b) |
| 10 | CH$_3$S | CH$_3$ | CH$_3$ | 165 | (c) |
| 11 | C$_2$H$_5$S | CH$_3$ | CH$_3$ | 131 | (c) |
| 12 | n-C$_3$H$_7$S | CH$_3$ | CH$_3$ | 102 | (c) |
| 13 | i-C$_3$H$_7$S | CH$_3$ | CH$_3$ | 129 | (c) |
| 14 | n-C$_4$H$_9$S | CH$_3$ | CH$_3$ | 98 | (c) |
| 15 | CH$_3$SO$_2$ | CH$_3$ | CH$_3$ | 186° | (c) |

The following are Examples of the preparation of 5-hydroxyhydantoins of formula (II) used as starting compounds in some of the above Examples.

EXAMPLE 1a (first part)

1-Methyl-3-(5-tert.-butyl-1,3,4-thiadiazol-2-yl)-parabanic acid

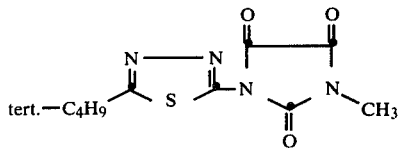

141 g (1.1 mols) of oxalyl chloride were added dropwise over the course of 1.1 hours to a suspension of 216 g (1 mol) of 1-methyl-3-(5-tert.-butyl-1,3,4-thiadiazol-2-yl)-urea in 1.5 liters of absolute toluene at 30° C. Thereafter the mixture was heated under reflux until the evolution of HCl had ceased. After cooling, the product was filtered off and washed with toluene.

Melting point: 165° C. (from methanol).

EXAMPLE 1a (second part)

1-methyl-3-(5-tert.-butyl-1,3,4-thiadiazol-2-yl)-5-hydroxy-hydantoin

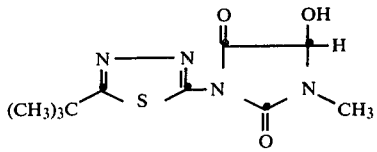

2.2 g (0.058 mol) of sodium borohydride were slowly introduced, in portions, into a suspension of 53.6 g (0.2 mol) of 1-methyl-3-(5-tert.-butyl-1,3,4-thiadiazol-2-yl)-parabanic acid in 150 ml of methanol at 0° C. After half the hydride had been added, a clear solution formed. Thereafter, the end product began to crystallize. The mixture was stirred for a further 30 minutes at 0° C. and subsequently cooled to between −5° and 10° C. The product was filtered off, rinsed with ice-cold methanol and dried in vacuo at 40° C.

1-Methyl-3-(5-tert.-butyl-1,3,4-thiadiazol-2-yl)-5-hydroxyhydantoin of melting point 163°–164° C. (from methanol) was obtained.

EXAMPLE 2a (first part)

1-Methyl-3-(5-ethylthio-1,3,4-thiadiazol-2-yl)-parabanic acid 114.5 g (0.902 mol) of oxalyl chloride were added dropwise over the course of one hour to a suspension of 178.9 g (0.82 mol) of 1-methyl-3-(5-ethylthio-1,3,4-thiadiazol-2-yl)-urea in 1.1 l of absolute toluene at 30° C. Thereafter, the mixture was heated under reflux until the evolution of HCl had ceased. After cooling, the product was filtered and rinsed with toluene.

Melting point: 136° C. (from ethyl acetate).

EXAMPLE 2a (second part)

1-Methyl-3-(5-ethylthio-1,3,4-thiadiazol-2-yl)-5-hydroxyhydantoin

This compound was obtained from the parabanic acid derivative prepared above by a procedure analogous to that of the second part of Example 1a. The product had a melting point of 144°–145° C.

The 5-hydroxyhydantoins listed below can be prepared analogously:

(II)

| Example | R | R¹ | Melting point (°C.) |
|---|---|---|---|
| (4a) | t-C$_4$H$_9$ | C$_2$H$_5$ | 167 |
| (8a) | CF$_3$ | CH$_3$ | 171–172 |
| (10a) | CH$_3$S | CH$_3$ | 204–205 |
| (12a) | n-C$_3$H$_7$S | CH$_3$ | 154 |
| (13a) | i-C$_3$H$_7$S | CH$_3$ | 139 |
| (14a) | n-C$_4$H$_9$S | CH$_3$ | 143 |
| (15a) | CH$_3$SO$_2$ | CH$_3$ | 226 |

The following may be mentioned individually as new active compounds of formula (I):

1-methyl-3-(5-tert.-butyl-1,3,4-thiadiazol-2-yl)-5-acetoxy-hydantoin,
1-ethyl-3-(5-tert.-butyl-1,3,4-thiadiazol-2-yl)-5-acetoxy-hydantoin,
1-methyl-3-(5-tert.-butyl-1,3,4-thiadiazol-2-yl)-5-propionyloxy-hydantoin,
1-ethyl-3-(5-tert.-butyl-1,3,4-thiadiazol-2-yl)-5-propionyloxy-hydantoin,
1-ethyl-3-(5-tert.-butyl-1,3,4-thiadiazol-2-yl)-5-methoxycarbonyloxy-hydantoin,
1-methyl-3-(5-tert.-butyl-1,3,4-thiadiazol-2-yl)-5-ethoxycarbonyloxy-hydantoin,
1-methyl-3-(5-tert.-butyl-1,3,4-thiadiazol-2-yl)-5-methylcarbamoyloxy-hydantoin, 1-ethyl-3-(5-tert.-butyl-1,3,4-thiadiazol-2-yl)-5-methylcarbamoyloxy-hydantoin,
1-methyl-3-(5-trifluoromethyl-1,3,4-thiadiazol-2-yl)-5-acetoxy-hydantoin,
1-methyl-3-(5-trifluoromethyl-1,3,4-thiadiazol-2-yl)-5-propionyloxy-hydantoin,
1-methyl-3-(5-trifluoromethyl-1,3,4-thiadiazol-2-yl)-5-methylcarbamoyloxy-hydantoin,
1-methyl-3-(5-trifluoromethyl-1,3,4-thiadiazol-2-yl)-5-ethylcarbamoyloxy-hydantoin,
1-methyl-3-(5-trifluoromethyl-1,3,4-thiadiazol-2-yl)-5-benzoyloxy-hydantoin,
1-methyl-3-(5-trifluoromethyl-1,3,4-thiadiazol-2-yl)-5-(3-chlorobenzoyl)-oxy-hydantoin,
1-methyl-3-(5-trifluoromethyl-1,3,4-thiadiazol-2-yl)-5-(4-methylbenzoyl)-oxy-hydantoin,
1-methyl-3-(5-methylmercapto-1,3,4-thiadiazol-2-yl)-5-acetoxy-hydantoin,
1-ethyl-3-(5-methylmercapto-1,3,4-thiadiazol-2-yl)-5-acetoxy-hydantoin,
1-methyl-3-(5-ethylmercapto-1,3,4-thiadiazol-2-yl)-5-acetoxy-hydantoin,
1-methyl-3-(5-propylmercapto-1,3,4-thiadiazol-2-yl)-5-acetoxy-hydantoin,
1-methyl-3-(5-isopropylmercapto-1,3,4-thiadiazol-2-yl)-5-acetoxy-hydantoin,
1-methyl-3-(5-butylmercapto-1,3,4-thiadiazol-2-yl)-5-acetoxy-hydantoin,
1-methyl-3-(5-methylsulfonyl-1,3,4-thiadiazol-2-yl)-5-acetoxy-hydantoin,
1-methyl-3-(ethylsulfonyl-1,3,4-thiadiazol-2-yl)-5-acetoxy-hydantoin, and
1-methyl-3-(5-isopropylsulfonyl-1,3,4-thiadiazol-2-yl)-5-acetoxy-hydantoin.

The active compounds according to the invention are distinguished by an excellent herbicidal activity and can therefore be employed successfully for combating weeds.

Weeds in the broadest sense are plants which grow in places where they are not desired. As weeds there may be mentioned: dicotyledons such as mustard (Sinapis), cress (Lepidium), cleavers (Galium), chickweed (Stellaria), camomile (Matricaria), gallant soldier (Galinsoga), goosefoot (Chenopodium), annual nettle (Urtica), and groundsel (Senecio) and monocotyledons such as timothy (Phleum), bluegrass (Poa), fescue (Festuca), goosegrass (Eleusine), foxtail (Setaria), ryegrass (Lolium) and barnyard grass (Echinochloa).

The active compounds according to the invention influence plant growth very strongly but in different ways so that they can be used as selective herbicides. They display particular advantages as selective herbicides in crops of cotton and cereals (including corn). When used in higher amounts and at higher concentrations (more than 10 kg/ha) the active compounds according to the invention are also suitable for the total combating of weeds.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents, and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperature and pressures, e.g., aerosol propellants, such as halogenated hydrocarbons, e.g., freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin, sulfite waste liquors and methyl cellulose.

The active compounds according to the invention can be used as a mixture with other active compounds.

The formulations in general contain from 0.1 to 95 percent by weight of active compound, preferably 0.5 to 90 percent by weight.

The active compounds can be employed as such or in the form of their formulations or the application forms prepared therefrom, such as ready-to-use solutions, emulsions, suspensions, powders, pastes and granules. They may be applied in the customary manner, for example by watering, spraying, atomizing, scattering or dusting.

They can be applied either according to the post-emergence method or according to the pre-emergence method; they are preferably applied after the emergence of the plants.

The amount of active compound employed can vary within substantial ranges. It essentially depends on the nature of the desired effect. In general, the amounts applied are from 0.1 to 25 kg/ha, preferably 0.5 to 10 kg/ha, of an area of agriculture.

The invention therefore provides a herbicidal composition containing as active ingredient a compound according to the invention in admixture with a solid or liquefied gaseous diluent or carrier or in admixture with a liquid diluent or carrier containing a surface-active agent.

The invention also provides a method of combating weeds which comprises applying to the weeds or their habitat a compound according to the invention alone or in the form of a composition containing an active ingredient a compound according to the invention in admixture with a diluent or carrier.

The invention also provides methods of obtaining crops protected from damage by weeds by being grown in areas in which, immediately prior to and/or during the time of the growing, a compound according to the invention was applied alone or in admixture with a diluent or carrier. It will be seen that the usual methods of providing a harvested crop may be improved by the present invention.

The compounds according to the invention, and the preparation and use of the compounds according to the invention, are illustrated by the following Examples.

EXAMPLE A

Post-emergence test

Solvent: 5 parts by weight of acetone
Emulsifier: 1 part by weight of alkylaryl polyglycol ether To produce a suitable preparation of active compound, one part by weight of active compound was mixed with the stated amount of solvent, the stated amount of emulsifier was added and the concentrate was then diluted with water to the desired concentration.

Test plants which had a height of 5–15 cm were sprayed with a preparation of the active compound in such a way that the amounts of active compound per unit area which were indicated in the table are applied. Depending on the concentration of the spray liquor, the amount of water used was between 1,000 and 2,000 liters per hectare. After three weeks, the degree of damage to the plants was determined and characterized by the values 0–5, which have the following meaning:

0—no effect
1—a few slightly burnt spots
2—marked damage to leaves
3—some leaves and parts of stalks partially dead
4—plant partially destroyed
5—plant completely dead.

The active compounds, amounts used and results can be seen from Table A.

Table A

| Active compound | Amount of active compound used, kg/ha | Echino-chloa | Cheno-podium | Sina-pis | Galin-soga | Stell-aria | Urtica | Oats | Cotton | Wheat |
|---|---|---|---|---|---|---|---|---|---|---|
| (3) | 1 | 4–5 | 5 | 5 | 5 | 5 | 5 | 4 | 3 | 4 |
|  | 0.5 | 3–4 | 5 | 5 | 5 | 5 | 4–5 | 3 | 2 | 3 |
| (10) | 1 | 5 | 5 | 5 | 5 | 5 | 5 | 4–5 | 5 | 3–4 |
|  | 0.5 | 4–5 | 5 | 5 | 5 | 4 | 4 | 3 | 2 | 2 |
| (11) | 1 | 5 | 5 | 5 | 5 | 5 | 3 | 4 | 1 | 3 |
|  | 0.5 | 5 | 5 | 5 | 5 | 4 | 2 | 3 | 0 | 3 |
| (12) | 1 | 5 | 5 | 5 | 3 | 4–5 | 2 | 4 | 1 | 1 |
|  | 0.5 | 4 | 4 | 4–5 | 2 | 2–3 | 0 | 3 | 0 | 0 |
| (9) | 1 | 4 | 4–5 | 4–5 | 5 | 5 | 3 | 2 | 1 | 1 |
|  | 0.5 | 3 | 4 | 3 | 4 | 5 | 2 | 1 | 0 | 0 |
| (1) | 1 | 5 | 5 | 5 | 5 | 5 | 5 | 4–5 | 3 | 3 |
|  | 0.5 | 5 | 5 | 5 | 3 | 5 | 5 | 4 | 2 | 2 |

Table A-continued

Post-emergence test

| Active compound | Amount of active compound used, kg/ha | Echino-chloa | Cheno-podium | Sina-pis | Galin-soga | Stell-aria | Urtica | Oats | Cotton | Wheat |
| --- | --- | --- | --- | --- | --- | --- | --- | --- | --- | --- |
|  (known) | 1<br>0.5 | 3<br>1 | 2<br>2 | 5<br>4 | 2<br>1 | 2<br>1 | 3<br>1 | 3<br>1 | 1<br>1 | 2<br>1 |

EXAMPLE B

Post-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the test plants were determined and characterized by the values 0-5, which have the following meaning:

0—no effect
1—slight damage or delay in growth
2—marked damage or inhibition of growth
3—heavy damage and only deficient development or only 50% emerged
4—plants partially destroyed after germination or only 25% emerged
5—plants completely dead or not emerged.

The active compounds, the amounts applied and the results obtained can be seen from Table B.

Table B

Pre-emergence test

| Active compound | Amount of active compound used, kg/ha | Echino-chloa | Cheno-podium | Sina-pis | Stell-aria | Galin-soga | Matri-caria | Oats | Cotton | Wheat | Corn |
| --- | --- | --- | --- | --- | --- | --- | --- | --- | --- | --- | --- |
| 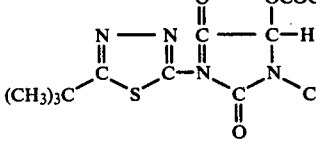 (3) | 5<br>2.5 | 5<br>4-5 | 5<br>5 | 5<br>4 | 5<br>5 | 5<br>5 | 5<br>5 | 3<br>2 | 3<br>2 | 0<br>0 | 0<br>0 |
| 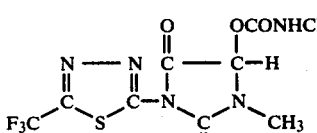 (9) | 5<br>2.5 | 5<br>4 | 5<br>4-5 | 5<br>4 | 5<br>4-5 | 5<br>5 | 5<br>5 | 1<br>0 | 1<br>0 | 0<br>0 | 1<br>0 |
| 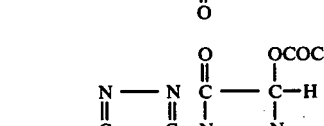 (1) | 5<br>2.5 | 5<br>4-5 | 5<br>5 | 5<br>5 | 5<br>5 | 5<br>5 | 5<br>5 | 4<br>3 | 1<br>0 | 2<br>1 | 3<br>2 |
| 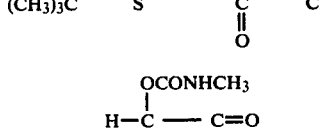 (known) | 5<br>2.5 | 4-5<br>2 | 3<br>3 | 5<br>4-5 | 2<br>2 | 5<br>5 | 4-5<br>4-5 | 3<br>2 | 2<br>1 | 2<br>2 | 2<br>2 |

It will be understood that the specification and examples are illustrative but not limitative of the present

What is claimed is:

1. 1-Methyl-3-(5-tert.-butyl-1,3,4-thiadiazol-2-yl-5-propionyloxy-hydantoin.

2. 1-Methyl-3-(5-tert.-butyl-1,3,4-thiadiazol-2-yl)-5-acetoxy-hydantoin.

3. Herbicidal compositions comprising a herbicidal acceptable carrier and in effective amounts at least one of 1-methyl-3-(5-tert.-butyl-1,3,4-thiadiazol-2-yl-5-propionyloxyhydantoin and 1-methyl-3-(5-tert.-butyl-1,3,4-thiadiazol-2-yl) -5-acetoxy-hydantoin a 3-(1,3,4-thiadiazol-2-yl)-5-acyloxy (carbamoyloxy)-hydantoin compound as claimed in claim 1.

4. Method of combating undesired vegetation which method comprises applying to said vegetation or to its habitat herbicidally effective amounts of at least one of 1-methyl-3-(5-tert.-butyl-1,3,4-thiadiazol-2-yl-5-propionyl-oxy-hydantoin and 1-methyl-3-(5-tert.-butyl-1,3,4-thiadiazol-2-yl) -5-acetoxy-hydantoin.

5. Method as claimed in claim 4 wherein said compound is applied to a crop cultivation containing weeds in amounts sufficient to destroy the weeds without substantial damage to the crops.

6. Method as claimed in claim 5 wherein said crop cultivation is cotton.

7. Method as claimed in claim 5 wherein said crop cultivation is corn.

8. Method as claimed in claim 5 wherein said compound is 1-methyl-3-(5-tert.-butyl-1,3,4-thiadiazol-2-yl)-5-propionyloxy-hydantoin.